United States Patent [19]

Suhonen

[11] Patent Number: 5,017,363

[45] Date of Patent: May 21, 1991

[54] STABILIZED STANNOUS FLUORIDE TOOTHPASTE

[75] Inventor: Christopher H. Suhonen, San Jose, Calif.

[73] Assignee: Gillette Canada, Inc., Montreal, Canada

[21] Appl. No.: 557,880

[22] Filed: Jul. 25, 1990

Related U.S. Application Data

[62] Division of Ser. No. 437,470, Nov. 15, 1989, Pat. No. 4,961,924.

[51] Int. Cl.$^5$ .................. A61K 7/18; A61K 33/16
[52] U.S. Cl. ............................ 424/52; 424/673
[58] Field of Search ........................ 424/52, 673

[56] References Cited

U.S. PATENT DOCUMENTS

| | | | |
|---|---|---|---|
| Re. 31,787 | 1/1985 | Chang | 424/52 |
| 3,429,963 | 2/1969 | Shedlovsky | 424/56 |
| 3,956,480 | 5/1976 | Dichter et al. | 424/49 |
| 4,138,477 | 2/1979 | Gaffar | 424/52 |
| 4,183,914 | 1/1980 | Gaffar et al. | 424/49 |
| 4,217,342 | 8/1980 | Gaffar et al. | 424/49 |
| 4,217,343 | 8/1980 | Gaffar et al. | 424/49 |
| 4,243,658 | 1/1981 | Chang | 424/52 |
| 4,296,096 | 10/1981 | Pierce | 424/52 |
| 4,304,766 | 12/1981 | Chang | 424/52 |
| 4,348,378 | 9/1982 | Kosti | 424/52 |
| 4,366,146 | 12/1982 | Chang | 424/52 |
| 4,459,277 | 7/1984 | Kosti | 424/49 |
| 4,470,964 | 9/1984 | Chang | 424/52 |
| 4,485,090 | 11/1984 | Chang | 424/52 |
| 4,510,127 | 4/1985 | Chang | 424/52 |
| 4,537,765 | 8/1985 | Gaffar et al. | 424/52 |
| 4,590,064 | 5/1986 | Gaffar | 424/52 |
| 4,627,977 | 12/1986 | Gaffar et al. | 424/52 |
| 4,661,341 | 4/1987 | Benedict et al. | 424/49 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,822,599 | 4/1989 | Mitra | 424/52 |
| 4,842,847 | 6/1989 | Amjad | 424/52 |
| 4,846,650 | 7/1989 | Benedict et al. | 424/49 |
| 4,847,070 | 7/1989 | Pyrz et al. | 424/52 |
| 4,869,898 | 9/1989 | Gaffar et al. | 424/52 |
| 4,871,531 | 10/1989 | Hartlaub et al. | 424/52 |
| 4,877,603 | 10/1989 | Degenitdardt et al. | 424/52 |
| 4,880,619 | 11/1989 | Gaffar | 424/52 |
| 4,889,712 | 12/1989 | Gaffar | 424/52 |
| 4,889,713 | 12/1989 | Gaffar et al. | 424/52 |
| 4,892,724 | 1/1990 | Amjad | 424/52 |
| 4,892,725 | 1/1990 | Amjad | 424/52 |
| 4,902,497 | 2/1990 | Crisanti et al. | 424/52 |
| 4,906,456 | 3/1990 | Gaffar et al. | 424/52 |
| 4,915,937 | 4/1990 | Amjad | 424/52 |
| 4,921,692 | 5/1990 | Gaffar et al. | 424/52 |
| 4,921,693 | 5/1990 | Gaffar et al. | 424/52 |
| 4,923,684 | 5/1990 | Ibrahim et al. | 424/52 |
| 4,925,654 | 5/1990 | Gaffar et al. | 424/52 |
| 4,931,273 | 6/1990 | Gaffar et al. | 424/52 |

OTHER PUBLICATIONS

Duperon et al., Chem. Abstr. 93:160933e (1980) J. Pedod. (1980) 4(4) 287-294 Release and Enamel Uptake of Fluoride from a Fluoride-Containing Polycarboxylate Cement (Contg 8% $SaF_2$ (Poly F Amalgamated Dental).

Swansun et al., Chem. Abstr 100:132555c (1984) J. Ural Rehabil (1984) 11(1): 53-63 (70% $SaF_2$ in Durclon (Polycarboxylate Cement).

*Primary Examiner*—Shep K. Rose
*Attorney, Agent, or Firm*—William B. Walker

[57] ABSTRACT

Stannous fluoride containing toothpaste compositions including an alkyl vinyl ether and maleic anhydride or acid copolymer as a stabilizing agent for stannous fluoride and methods for preparing such stabilized compositions.

5 Claims, No Drawings

STABILIZED STANNOUS FLUORIDE TOOTHPASTE

RELATIONSHIP TO COPENDING APPLICATION

This application is a Division of copending application Ser. No. 07/437,470 filed Nov. 15, 1989 now U.S. Pat. No. 4,961,924. Other related copending applications are applications Ser. No. 07/437,469, now U.S. Pat. No. 4,970,065, Ser. No. 07/437,467, now U.S. Pat. No. 4,960,586, Ser. No. 07/557,881 filed concurrently herewith and Ser. No. 07/557,882 filed concurrently herewith.

FIELD OF THE INVENTION

This invention relates to a stannous fluoride toothpaste with improved stability. In particular, this invention is directed to an aqueous toothpaste composition comprising stannous fluoride stabilized with a copolymer of maleic anhydride or acid and a lower alkyl vinyl ether.

BACKGROUND OF THE INVENTION

Stannous fluoride has been used in oral care products since the early 1950's, and stannous fluoride has been reported to be an effective agent for treating various oral conditions and diseases including plaque, gingivitis, sensitivity, enamel decalcification, and periodontitis, among others. Product stability is an outstanding problem because stannous fluoride is unstable in water and forms stannous oxy-fluoride and stannic compounds, both of which reduce or inhibit enamel fluoridation, that is, formation of stannous fluorophosphate and fluoroapatite. This instability has required the withdrawal and reformulation of the original stannous fluoride toothpaste as a sodium fluoride composition. It has required that stannous fluoride products be formulated as non-aqueous compositions such as powders and non-aqueous gels in moisture-free conditions. Despite highly specialized precautionary measures during formulation of oral care products, significant variations are found in stannous ion concentrations of commercial dentifrice gel products among different manufacturers as well as among batches of the same brand of dentifrice because of stannous ion instability.

DESCRIPTION OF THE PRIOR ART

The original aqueous stannous fluoride toothpastes have been reformulated as stannous ion-free compositions because of the instability of the stannous ion in water. Numerous stannous fluoride formulations with "stabilizing agents" have been proposed.

U.S. Pat. No. 3,445,567 claims that aqueous stannous fluoride compositions can be stabilized with sorbitol or a mixture of sorbitol and glycerine. However, this composition lacks the shelf-life stability required for commercial use.

U.S. Pat. Nos. 3,711,604, 3,919,409, 3,935,306 and 3,980,767 disclose toothpaste and dentifrice formulations including soluble fluoride compounds, including stannous fluoride. The toothpaste formulations use a variety of standard ingredients and gelling agents including carboxyvinyl polymers sold under the tradename Carbopol and insoluble abrasives such as silica and silicates. The stannous fluoride containing embodiments disclosed in these patents lack the stability found in the compositions of this invention.

U.S. Pat. No. 4,418,057 describes another approach. Stannous fluoride is formulated as a non-aqueous gel mixture including anhydrous glycerin and hydroxyethyl cellulose gelling agent. Total exclusion of moisture from the moisture is required to protect the stannous ion.

U.S. Pat. No. 4,259,316, while noting the instability of stannous fluoride, proposes a compositions containing phytic acid for inhibiting dental caries. Both dry dentrifices and aqueous formulations are described. If protected from moisture, the dentrifices would appear to retain the stannous ion in efficacious form. The stannous ion would rapidly convert to the ineffective oxy-stannous or stannate forms upon exposure to moisture in solution or in the oral cavity. Apparently, excess amounts of stannous fluoride are added in an effort to offset the loss of stannous ion. However, this requires the exposure of the user to excessive, unsafe levels of stannous ion.

EPO application No. 88308337.0 (Publication No. 0 311 260 A3) published Apr. 12, 1989 describes compositions containing stannous fluoride, and as a stannous reservoir to replace stannous ion lost through degradation, stannous gluconate. Listed as suitable abrasive polishing agents are silicas, including gels and precipitates; insoluble sodium polymetaphosphate; $\beta$-phase calcium pyrophosphate; alumina and resinous abrasive materials which do not contribute soluble calcium ions which form complexes with the fluoride ion. Calcium carbonate, calcium phosphate and regular calcium pyrophosphate are excluded.

U.S. Pat. No. 4,254,101 describes toothpastes containing a humectant, silica abrasive, a carboxyvinyl polymer, water and fluoride compounds as optional ingredients. The only carboxyvinyl polymers disclosed are colloidally water-soluble polymers of acrylic acid crosslinked with polyallyl sucrose or polyallyl pentaerythritol. A variety of fluoride compounds including sodium fluoride are described as suitable optional ingredients. Stannous fluoride is included in the list of suitable fluoride compounds although no suggestion is made about its instability or that it could be used as an effective source of stannous ion. It is presented as equivalent to sodium fluoride as a source of fluoride ion. Phosphorus-containing anticalculus agents are also listed as optional ingredients.

U.S. Pat. No. 4,515,772 describes oral compositions including dentrifices and aqueous compositions including toothpastes and mouthwashes containing certain pyrophosphate salts as anticalculus formulations. In the prior art description, it lists a number of chelating agents proposed as anticalculus agents, including EDTA (ethylenediaminetetraacetic acid), nitrilotriacetic acid, polyphosphonates and fluoride, and carbonyl diphosphonates. The patent lists as suitable abrasives silica, calcium pyrophosphate, $\beta$-phase pyrophosphate, alumina and other materials. A comprehensive list of fluoride ion sources are listed. Stannous fluoride is included in the list although no suggestion is made about its instability or that it could be used as an effective source of stannous ion. A variety of flavoring agents are disclosed. Included in a list of binders are gums and carboxyvinyl polymers.

U.S. Pat. No. 3,956,479 describes use of quaternary anticalculus compounds in dental creams, tables or powders containing polishing agents such as water-insoluble phosphates, binders, detergents, gelling agents, flavoring agents, and fluoride-containing compounds such as sodium fluoride, stannous fluoride and sodium monofluorophosphate.

U.S. Pat. No. 4,627,977 describes oral compositions containing a calculus-inhibiting amount of a linear molecularly dehydrated polyphosphate salt, and to inhibit hydrolysis of the polyphosphate salt in the saliva, a combination of a fluoride ion-providing source and a synthetic linear polymeric polycarboxylate. Included in the list of suitable polycarboxylates are copolymers of maleic anhydride or acid and ethylenically unsaturated monomers including alkyl vinyl ethers available as Grantrez AN 139, AN 119, and S97. An extensive list of fluoride ion sources are provided, including sodium and stannous fluorides and sodium monofluorophosphate. An extensive list of polishing agents are provided including water-insoluble phosphates, silicates and silicas, bentonites and inorganic polishing agents. Silicas are listed as preferred.

A. Gaffar et al in *Compend.Contin.Educ.Dent, Suppl.* No. 8, 242-250 (1987) and Thomas G. Schiff in *Compend.Contin.Educ.Dent, Suppl.* No. 8, 275-277 (1987) describe evaluations of pyrophosphate compositions containing sodium fluoride and a copolymer of methoxyethylene and maleic anhydride known as GANTREZ® as anticalculus dentifrices. The oral cavity contains enzymes which attack and degrade the pyrophosphates, rapidly removing their anticalculus activity. The enzymes require soluble magnesium ion for activity. The copolymer is provided to complex magnesium ions, making them unavailable to the enzymes and thus inhibiting their activity. Its purpose is to protect the pyrophosphates and maintain their anticalculus activity.

SUMMARY AND OBJECTS OF THE INVENTION

The present invention provides an aqueous toothpaste composition containing stannous fluoride in combination with a stannous ion chelating copolymer of an alkyl vinyl ether and maleic anhydride or acid in an amount to effectively stabilize the stannous ion. The composition preferably contains from 10 to 30 weight percent water, from 0.05 to 5 and preferably from 0.5 to 5 weight percent of the chelating copolymer and from 0.05 to 5 and preferably from 0.3 to 0.5 weight percent stannous fluoride and an insoluble abrasive agent. The weight ratio of stannous fluoride to copolymer is preferably between 0.01 to 1.0. The composition is substantially free from silica, soluble phosphates such as soluble pyrophosphates (i.e., tetrasodium pyrophosphate, tetrapotassium phosphates, etc.), and aldehyde group containing compounds.

The method of this invention for formulating an aqueous toothpaste including stannous fluoride comprises the step of dispersing the stannous fluoride in an aqueous solution of an alkyl vinyl ether and maleic anhydride or acid copolymer, the amount of said copolymer being sufficient to stabilize the stannous fluoride concentration during formulation.

It is an object of this invention to provide a stannous fluoride toothpaste formulation which is "effectively stabilized", that is, the stannous fluoride concentration in the product after three months at forty-five degrees centigrade remains at an acceptable therapeutic level. Product stability after three months at forty-five degrees centigrade is comparable to product stability after three years at room temperature.

DETAILED DESCRIPTION OF THE INVENTION

The essential ingredients of the compositions of this invention are stannous fluoride and the stannous ion chelating copolymer in an effectively stabilizing amount.

The term "effectively stabilized" and "effectively stabilizing amount" is defined to mean that the stannous ion concentration, expressed as stannous fluoride, after three months storage under the conditions described in Example 2 is equivalent to about 70 percent or more of the original concentration of stannous ion at the time of formulation.

The composition contains from 10 to 30 weight percent water, from 0.05 to 5 and preferably from 0.5 to 5 weight percent of the chelating copolymer and from 0.05 to 5 and preferably from 0.3 to 0.5 weight percent stannous fluoride and an insoluble abrasive agent.

The stannous ion stabilizing copolymer is a copolymer of maleic anhydride or acid and a polymerizable ethylenically unsaturated monomer, preferably a lower alkyl vinyl ether such as methoxyethylene, having a molecular weight of from about 30,000 to 1,000,000. The mole ratios of the maleic anhydride or acid to the ethylenically unsaturated monomer is preferably from 1:4 to 4:1. Suitable polymers are available from GAF under the tradename GANTREZ TM and are disclosed in U.S. Pat. No. 4,627,977, the entire contents of which are hereby incorporated by reference. These copolymers have the unique ability to form chelates with the stannous ion which are sufficiently strong to provide oxidation protection to the stannous ion while being sufficiently weak to not remove calcium from the tooth structure. EDTA and other strong chelating agents are undesirable because they deplete calcium from the tooth enamel.

The term "lower alkyl" is defined to be a straight or branch-chained hydrocarbon group having from 1 to 6 carbons and preferably from 1 to 4 carbons and including methyl, ethyl, propyl, isopropyl, butyl, isobutyl, t-butyl, pentyl and hexyl groups.

The toothpaste formulation contains one or more abrasive agents (other than silica or silicates) and can contain other conventional ingredients to impart the desired consistency, texture, resistance to hardening, flavor and the like.

Suitable abrasive agents include insoluble phosphates such as calcium pyrophosphate, $\beta$-phase pyrophosphate, and alkali metal metaphosphates. We have discovered that the stabilizing function of the stannous ion chelating polymer is not effective in the presence of silica and silicates.

Any conventional humectant can be used. Suitable humectants include sorbitol, glycerin, propylene glycol, and other polyhydric alcohols; and the natural or synthetic gums conventionally used as hardening control agents and binders.

The compositions can also contain conventional flavoring agents which do not have an aldehyde group. We have discovered that aldehyde-containing flavoring agents such as cinnaldehyde, while not reacting directly with the stannous ion, interacts with the stannous ion chelating polymer, allowing stannous oxidation to occur.

The compositions should have a pH within the range of from 2 to 11 and preferably from 3 to 7.

The compositions can also contain other conventional components such as anti-foaming agents, anticariogenic agents, soluble fluoride compounds, surfactants, gelling agents, coloring or whitening agents, antibacterial agents, preservatives, chlorophyll compounds, and additional ammoniated materials which do not interfere with the stability of the stannous ion by reacting therewith or with the stannous ion chelating polymer. Suitable materials are described in U.S. Pat. Nos. 4,254,101 and 4,627,977, the entire contents of which are incorporated by reference in their entireties.

The formulations of this invention are manufactured using procedures which protect the stannous ion from oxidation. The stannous fluoride is initially dissolved in an aqueous solution containing the stannous chelating copolymer. This solution can be then mixed with other components by conventional procedures to form the toothpaste formulations of this invention. In a preferred procedure, a premix solution is prepared by dispersing from 0.5 to 26 weight percent stannous fluoride in water containing from 5.0 to 26 weight percent stannous ion stabilizing copolymer, the weight ratios of the stannous fluoride to copolymer being from 0.01 to 1.0 in the premix solution. The premix is then mixed with the other components of the toothpaste to provide the desired level of stannous fluoride. Additional protection from oxidation can be provided during manufacture by carrying out the procedures in an inert atmosphere.

For additional protection against the oxidation, the product should be stored in oxygen impermeable containers. Preferred containers are laminated tube such as GLAMINATE TM tubes (American Can Company). Suitable tubes are laminates of a flexible plastic such as a polyolefin (i.e., low density polyethylene, etc.) and an oxygen barrier layer such as an oxygen impermeable metal foil (i.e., aluminum foil). The laminates include other conventional layers such as adhesives (i.e., ethylene copolymers), paper or other non-woven fibrous materials, and the like. The layer exposed to the stannous fluoride toothpaste should be essentially free from toxic substances and materials which would be released into the toothpaste during manufacture, storage or use and impair the stability of the toothpaste composition.

Preferred formulations have the composition shown in Table A.

TABLE A

| Ingredients | Weight Percent |
|---|---|
| Purified Water USP | 10–30 |
| Carbopol[a] | 0.05–1.0 |
| Sodium CMC[b] | 0.1–2.0 |
| Glycerin 96% USP | 5.0–30 |
| Xanthan Gum (KELTROL) | 0.1–1.5 |
| Methylparaben NF | 0.1–5.0 |
| Propylparaben NF | 0.01–.10 |
| Polyethylene Glycol 400[c] | 0.1–4.0 |
| Stannous Chelating Copolymer | 0.5–5.0 |
| Stannous Fluoride | 0.3–0.5 |
| Sorbitol 70% USP | 10–35 |
| Sodium Saccharin USP Crystal | 0.05–0.5 |
| Calcium Pyrophosphate | 30–45 |
| Zinc Citrate | 0.1–2.0 |
| Insoluble Sodium Metaphosphate | 30–45 |
| Sodium Lauryl Sulfate Needles | 0.05–3.0 |
| Sodium Hydroxide NF (10% sol'n) | 0.5–5.0 |
| Flavor | 0.5–1.5 |

Carbopol[a] is a carboxyvinyl polymer available from B. F. Goodrich Company.
Sodium CMC[b] is carboxymethyl cellulose.
Polyethylene Glycol 400[c] is polyethylene glycol having a molecular weight of about 400, available from Union Carbide.

This invention is further described by the following specific but non-limiting examples. Percentages are weight percents unless otherwise indicated.

EXAMPLE 1

An aqueous solution containing methyl vinyl ether-maleic anhydride copolymer and percent stannous fluoride is prepared to form a stabilized stannous fluoride solution. This solution is mixed with the other ingredients listed in Table B below. The amounts of the ingredients are selected to yield a final toothpaste composition having the following composition:

TABLE B

| Ingredients | Weight Percent |
|---|---|
| Purified Water | 29.00 |
| Polyethylene Glycol 400 | 0.40 |
| Glycerin 96% USP | 5.00 |
| Methylparaben NF | 0.15 |
| Propylparaben NF | 0.05 |
| Copolymer[a] | 1.00 |
| Stannous Fluoride | 0.455 |
| Sodium Hydroxide (10% solution) | 4.50 |
| Sorbitol 70% USP | 16.275 |
| Sodium Saccharin USP Crystal | 0.20 |
| Calcium Pyrophosphate | 40.00 |
| Zinc Citrate | 0.40 |
| Glycerine 96% USP | 5.00 |
| Natural Mint Flavor A-1159 FELTON | 1.00 |
| Sodium Lauryl Sulfate Needles | 1.00 |

Copolymer[a] is the free acid of a methyl vinyl ether and maleic anhydride copolymer having a molecular weight of about 70,000, benzene-free, and sold under the tradename GANTREZ S-97BF by GAF Corporation.

EXAMPLE 2

Dentifrice compositions prepared as described in Example 1 and having the formulations shown in Table C were analyzed to determine the initial concentrations of stannous and fluoride ions achieved at formulation and to determine the initial ion concentrations after 1, 2, and 3 months storage at 45° C. in sealed oxygen impermeable tubes.

TABLE C

| Ingredients | Weight Percent | | | |
|---|---|---|---|---|
| | A | B | C | D |
| Purified Water | 29.00 | 29.00 | 29.00 | 29.00 |
| Carbopol 950 | 0.20 | 0.20 | 0.20 | 0.20 |
| Glycerin 96% USP | 10.00 | 10.00 | 10.00 | 10.00 |
| Xanthan Gum | 0.15 | 0.40 | 0.40 | 0.40 |
| Methylparaben NF | 0.15 | 0.15 | 0.15 | 0.15 |
| Propylparaben NF | 0.02 | 0.02 | 0.02 | 0.02 |
| Copolymer[a] | 1.00 | 1.00 | 1.00 | 1.00 |
| Stannous Fluoride | 0.455 | 0.455 | 0.455 | 0.455 |
| Sodium Hydroxide (10% solution) | 4.50 | 4.50 | 4.50 | 4.50 |
| Sorbitol 70% USP | 21.225 | 10.275 | 16.675 | 16.675 |
| Sodium Saccharin USP Crystal | 0.20 | 0.20 | 0.20 | 0.20 |
| Calcium Pyrophosphate | 30.00 | 35.00 | 35.00 | 35.00 |
| Zinc Citrate | 0.80 | 0.80 | 0.40 | 0.40 |
| Natural Mint Flavor A-1159 FELTON | 1.00 | 1.00 | | |
| Doublemint Flavor #30672 Noville | | | 1.00 | 1.00 |

TABLE C-continued

| Ingredients | Weight Percent | | | |
|---|---|---|---|---|
| | A | B | C | D |
| Sodium Lauryl Sulfate Needles | 1.00 | 1.00 | 1.00 | 1.00 |

Copolymer[a] is the free acid of a methyl vinyl ether and maleic anhydride copolymer having a molecular weight of about 70,000, benzene-free, and sold under the tradename GANTREZ S-97BF by GAF Corporation.

The following results were obtained, concentrations being reported as weight percents.

| Time | Sn as $SnF_2$ | F as $SnF_2$ | pH |
|---|---|---|---|
| Formulation A | | | |
| Initial | 0.453 | 0.420 | 5.2 |
| one month | 0.435 | 0.439 | 5.2 |
| two months | 0.458 | 0.428 | 5.1 |
| three months | 0.412 | 0.414 | 5.2 |
| Formulation B | | | |
| Initial | 0.479 | 0.430 | 5.1 |
| one month | 0.444 | 0.442 | 5.1 |
| two months | 0.402 | 0.398 | 5.2 |
| three months | 0.433 | 0.353 | 5.2 |
| Formulation C | | | |
| Initial | 0.454 | 0.452 | 5.3 |
| one month | 0.439 | 0.472 | 5.2 |
| two months | 0.468 | 0.472 | 5.2 |
| three months | 0.477 | 0.469 | 5.3 |
| Formulation D | | | |
| Initial | 0.447 | 0.429 | 5.7 |
| one month | 0.443 | 0.440 | 5.6 |
| two months | 0.455 | 0.420 | 5.8 |
| three months | 0.458 | 0.441 | 5.8 |

EXAMPLE 3

Dentifrice compositions prepared as described in Example 1 and having the formulations shown in Table D were analyzed to determine the initial concentrations of stannous and fluoride ions achieved at formulation and to determine the initial ion concentrations after 1, 2, and 3 months storage at 45° C. in sealed oxygen impermeable tubes.

TABLE D

| Ingredients | Weight Percent | | | | |
|---|---|---|---|---|---|
| | E | F | G | H | I |
| Purified Water | 29.50 | 22.50 | 29.50 | 24.50 | 17.00 |
| Carbopol 950 | 0.30 | | 0.20 | 0.20 | |
| Glycerin 96% USP | 10.00 | 10.00 | 10.00 | 10.00 | 10.00 |
| Xanthan Gum | 0.50 | 0.60 | 0.80 | 0.80 | 0.70 |
| Carboxymethyl Cellulose | | 0.40 | | | 0.30 |
| Methylparaben NF | 0.15 | 0.15 | 0.15 | 0.15 | 0.15 |
| Propylparaben NF | 0.02 | 0.02 | 0.02 | 0.02 | 0.02 |
| Copolymer[a] | 1.00 | 1.00 | 1.00 | 1.00 | 1.00 |
| Stannous Fluoride | 0.455 | 0.455 | 0.455 | 0.455 | 0.43 |
| Sodium Hydroxide (10% solution) | 4.50 | 3.00 | 4.50 | 4.00 | 3.00 |
| Sorbitol 70% USP | 14.975 | 24.275 | 14.975 | 15.875 | 24.40 |
| Sodium Saccharin USP Crystal | 0.20 | 0.20 | 0.20 | 0.20 | 0.20 |
| Calcium Pyrophosphate | 35.00 | 35.00 | 35.00 | 40.00 | 40.00 |
| Zinc Citrate | 0.40 | 0.40 | 0.40 | 0.80 | 0.80 |
| Tween-80[b] | 1.0 | | | | |
| Pluronic F127[c] | | | 0.80 | | |
| Mint Flavor A-1159 FELTON | 0.8 | 0.8 | 0.80 | 1.00 | 1.00 |
| Sodium Lauryl Sulfate Needles | 1.2 | 1.2 | 1.2 | 1.00 | 1.00 |

Copolymer[a] is the free acid of a methyl vinyl ether and maleic anhydride copolymer having a molecular weight of about 70,000, benzene-free, and sold under the tradename GANTREZ S-97BF by GAF Corporation.
Tween-80[b] is polyoxyethylenesorbitan monooleate.
Pluronic F127[c] is a condensate of ethylene oxide with propylene oxide condensates of propylene glycol.

The following results were obtained, concentrations being reported as weight percents.

| Time | Sn as $SnF_2$ | F as $SnF_2$ | pH |
|---|---|---|---|
| Formulation E | | | |
| Initial | 0.462 | 0.453 | 5.6 |
| one month | 0.432 | 0.449 | 5.6 |
| two months | 0.453 | 0.444 | 5.4 |
| three months | 0.431 | 0.453 | 5.4 |
| Formulation F | | | |
| Initial | 0.471 | 0.435 | 5.2 |
| one month | 0.390 | 0.441 | 5.2 |
| two months | 0.415 | 0.436 | 5.0 |
| three months | 0.418 | 0.429 | 5.0 |
| Formulation G | | | |
| Initial | 0.456 | 0.449 | 5.8 |
| one month | 0.445 | 0.439 | 5.7 |
| two months | 0.451 | 0.449 | 5.5 |
| three months | 0.454 | 0.430 | 5.4 |
| Formulation H | | | |
| Initial | 0.462 | 0.460 | 5.4 |
| one month | 0.464 | 0.438 | 5.1 |
| two months | 0.459 | 0.440 | 5.1 |
| three months | 0.450 | 0.445 | 4.9 |
| Formulation I | | | |
| Initial | 0.469 | 0.438 | 5.2 |
| one month | 0.396 | 0.407 | 4.9 |
| two months | 0.414 | 0.410 | 4.9 |
| three months | 0.398 | 0.409 | 4.6 |

EXAMPLE 4

The following Example illustrates the stabilizing effect of the alkyl vinyl ether/maleic anhydride copolymers on stannous fluoride in an aqueous environment such as encountered during formulation of stannous fluoride containing oral care products. Two sample solutions of 0.455 percent by weight stannous fluoride in deionized water were prepared. In the first sample solution, the stannous fluoride was added to the deionized water. In a second sample solution, the stannous fluoride was added to a solution of 1 percent by weight of methyl vinyl ether-maleic anhydride copolymer in deionized water. In the first sample solution a precipitate of stannous oxides appeared almost immediately and the intensity of the precipitate increased with time. Analyses of the supernatant and sediment portions of centrifuged samples revealed that the concentration of stannous fluoride in the supernatant and sediment portions were 0.371 percent by weight and 0.099 percent by weight respectively. The second sample solution was clear and there was no evidence of precipitation. These results were confirmed by comparative sample analyses using a turbidity meter. Analyses of the supernatant and sediment portions of centrifuged samples revealed that the concentration of stannous fluoride in the supernatant was 0.456 percent by weight and no stannous fluoride was detected in the sediment portion.

What is claimed is:

1. An aqueous toothpaste composition consisting essentially of water-unstable stannous fluoride and a lower alkyl vinyl ether and maleic anhydride copolymer as the essential stannous ion chelate forming stabilizer in an amount sufficient to effectively stabilize the stannous fluoride concentration against stannous oxide precipitation by providing oxidation protection to the stannous ion, the composition being substantially free from soluble pyrophosphates, silica containing compounds, and aldehyde group containing compounds.

2. A composition of claim 1 where the lower alkyl vinyl ether is methyl vinyl ether.

3. A composition of claim 1 where the amount of stannous fluoride included in the composition provides between about 0.05 to about 5.0 percent by weight stannous fluoride, the copolymer being present in an amount between about 0.5 to about 5.0 percent by weight, the weight ratio of stannous fluoride to copolymer being from between about 0.01 to about 1.0.

4. A composition of claim 1 where the composition includes an abrasive.

5. A composition of claim 4 where the abrasive is a calcium pyrophosphate.

* * * * *